United States Patent
Mor et al.

(10) Patent No.: US 11,105,816 B2
(45) Date of Patent: *Aug. 31, 2021

(54) METHODS FOR IDENTIFICATION OF PREGNANCY FAILURE

(71) Applicant: Amir Mor, New Haven, CT (US)

(72) Inventors: Amir Mor, New Haven, CT (US); Hugh T. Taylor, Easton, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/681,924

(22) Filed: Nov. 13, 2019

(65) Prior Publication Data

US 2020/0096517 A1 Mar. 26, 2020

Related U.S. Application Data

(63) Continuation-in-part of application No. 15/951,187, filed on Apr. 12, 2018, now Pat. No. 10,509,043.

(60) Provisional application No. 62/486,467, filed on Apr. 18, 2017.

(51) Int. Cl.
*G01N 33/68* (2006.01)

(52) U.S. Cl.
CPC ..... *G01N 33/689* (2013.01); *G01N 2800/368* (2013.01)

(58) Field of Classification Search
CPC ........... G01N 33/689; G01N 2800/368; G01N 2333/471
See application file for complete search history.

(56) References Cited

U.S. PATENT DOCUMENTS

| | | |
|---|---|---|
| 2013/0157373 A1 | 6/2013 | Selinfreund et al. |
| 2017/0242023 A1 | 8/2017 | Iles et al. |

OTHER PUBLICATIONS

Seaward et al. (SAMT 1988 vol. 74, p. 289-290) (Year: 1988).*
Bennett et al. (British J. Obstetrics and Gynaecology 1978 vol. 85, p. 348-350) (Year: 1978).*
Clinical Practice Guideline (publication Dec. 2010). (Year: 2010).*
Mor et al. Obstetrics and Gynecology 2016 vol. 127, Supp. p. 141S.
Anai et al. Obstetrics and Gynecology 1997 vol. 89, p. 261-264.
Sarandakou A, Protonotariou E, Rizos D. Tumor markers in biological fluids associated with pregnancy. Crit Rev Clin Lab Sci 2007;44:151-78.
Mizejewski GJ. Levels of alpha-fetoprotein during pregnancy and early infancy in normal and disease states. Obstet Gynecol Surv 2003;58:804-26.
Doubilet PM, Benson CB, Bourne T, et al. Diagnostic criteria for nonviable pregnancy early in the first trimester. The New England journal of medicine 2013;369:1443-51.
Sajid M, Kawde A-N, Daud M. Designs, formats and applications of lateral flow assay: A literature review. Journal of Saudi Chemical Society 2015;19:689-705.
Kolte AM, Bernardi LA, Christiansen OB, Quenby S, Farquharson RG, Goddijn M, et al. Terminology for pregnancy loss prior to viability: a consensus statement from the ESHRE early pregnancy special interest group. Hum Reprod. 2015;30(3):495-8.

* cited by examiner

*Primary Examiner* — Changhwa J Cheu
(74) *Attorney, Agent, or Firm* — JMB Davis Ben-David

(57) ABSTRACT

Provided is a method for identifying and treating a pregnancy devoid of uterine fetal or embryonic tissue in a subject by determining a concentration of alpha-fetoprotein (AFP) in a specimen evacuated from the uterus of the subject; comparing the concentration of AFP to a reference value; wherein when the AFP concentration in the specimen evacuated from the uterus is below that of a reference value, absence of uterine fetal or embryonic tissue is indicated. Also provided is a method for identifying and treating a presence of fetal or embryonic tissue in a location of a subject other than the uterus by determining a concentration of AFP in a non-uterine specimen obtained from the subject; comparing the concentration of AFP in the specimen to a reference value; wherein when the AFP concentration in the specimen is above that of a reference value, presence of fetal or embryonic tissue is indicated.

17 Claims, 6 Drawing Sheets

METHODS FOR IDENTIFICATION OF PREGNANCY FAILURE

CROSS-REFERENCE TO RELATED APPLICATIONS

This is a Continuation-in-Part of U.S. patent application Ser. No. 15/951,187, filed Apr. 12, 2018, which in turn claims the benefit of U.S. Provisional Application No. 62/486,467, filed Apr. 12, 2017. The contents of the foregoing patent applications are incorporated by reference herein in their entirety.

FIELD OF THE INVENTION

The invention relates to the field of pregnancy failure, and more particularly, to a method for identification of pregnancy failure comprising comparing a concentration of at least one element of fetal or embryonic origin in the vaginal fluid of a subject to a reference concentration of the same element of fetal or embryonic origin. Further provided is a method for identification and treatment of a pregnancy devoid of uterine fetal or embryonic tissue in a subject comprising comparing a concentration of alpha-fetoprotein (AFP) in a specimen evacuated from a subject to a reference concentration.

BACKGROUND OF THE INVENTION

Pregnancy failure is common, occurring in about 12 to 15% of all clinically recognized pregnancies, and up to 22% of all pregnancies in the United States. Common risk factors include chromosomal abnormalities.

Common symptoms of pregnancy failure include vaginal bleeding and intrauterine cramping. However, such symptoms may also occur during normal gestation, especially during the first trimester.

Sonographic findings in early pregnancy may be inconclusive, and differentiating between intrauterine and extra-uterine pregnancies (IUP and EUP, respectively) is challenging.

Moreover, serial beta Human Chorionic Gonadotropin (β-HCG) measurements over time are oftentimes needed in order to differentiate between a normal and a failing pregnancy and therefore, may not be useful for same-day diagnosis.

It would therefore be desirable to have a simple, rapid and accurate method for identification of a pregnancy failure, that is devoid of at least some of the limitations of the prior art.

It would further be useful to have a simple, rapid and accurate method for method for identification of a pregnancy devoid of uterine fetal or embryonic tissue.

SUMMARY OF THE INVENTION

The invention, in some embodiments thereof, relates to a method for identification of pregnancy failure comprising comparing a concentration of at least one element of fetal or embryonic origin in the vaginal fluid of a subject to a reference concentration of the same element of fetal or embryonic origin.

The invention provides an effective, safe and non-invasive method for same-day detection of pregnancy failure, which may be used in early-stage pregnancy.

Aspects and embodiments of the invention are described in the specification herein below and in the appended claims.

Alpha-fetoprotein (AFP) is a glycoprotein produced by the embryonic yolk sac in early-stage pregnancy, and later on by the fetal liver.[1] In the first trimester, as early as the 5$^{th}$ week of gestation, AFP concentration can be measured from the embryonic tissue. It has been shown that AFP in the fetal serum is at least 1,000 times higher than in the maternal serum at any gestational age.[2]

The present Inventor have surprisingly found that an AFP concentration in the vaginal blood of a subject, which is relatively high when compared to the AFP concentration in the serum of the same subject indicates the presence of a pregnancy failure, particularly a failure of an intrauterine pregnancy.

According to an aspect of some embodiments of the invention, there is provided a method for identifying pregnancy failure in a subject, the method comprising determining a concentration of at least one element of fetal or embryonic origin in the vaginal fluid of the subject; and comparing the concentration of the at least one element of fetal or embryonic origin to a reference value, wherein when the concentration of the at least one element of fetal or embryonic origin in the vaginal fluid of the subject is higher than the reference value, pregnancy failure is indicated.

In some embodiments, the reference value is a concentration of said at least one element of fetal or embryonic origin in maternal serum of the same subject i.e. in the serum of the subject in whom pregnancy failure is to be identified.

In some embodiments, the reference value is a predetermined concentration value of said at least one element of fetal or embryonic origin and wherein pregnancy failure is indicated when a concentration of the element of fetal or embryonic origin in vaginal fluid of the subject is greater than the predetermined concentration value. Such a reference concentration is preferably determined as an average of maternal serum concentrations obtained from at least 30 reference subjects in the same trimester of pregnancy as the subject in whom pregnancy failure is to be identified.

In some embodiments, the vaginal fluid is vaginal blood.
In some embodiments, the vaginal fluid is physiological vaginal discharge As used herein, the term "element of fetal or embryonic origin" refers to a biochemical element originating from a fetus or embryo, such as a component of a tissue, a fluid, a protein, a carbohydrate, electrolytes, fatty acids, or nucleic acids.

In some embodiments, the element of fetal or embryonic origin is selected from the group consisting of a protein (such as a glycoprotein, an antibody, an enzyme, a hemoglobin component, an amyloid, cytoskeleton component, muscle component); a nucleic acid (such as deoxyribonucleic acid or ribonucleic acid), a vitamin, an electrolyte, phospholipids, fatty acids, hormones, an antigen and a carbohydrate (such as a sugar molecule, an antigen, such as a cell surface antigen). In some embodiments, the element of fetal or embryonic origin is a glycoprotein. In some such embodiments, the glycoprotein comprises AFP. In some embodiments, the element of fetal or embryonic origin is selected from the group consisting of carcinoembryonic antigen, squamous cell carcinoma antigen; prostate serum antigen; and hemoglobinA1C.

In some embodiments, the pregnancy failure is a failure of an intrauterine pregnancy.

In some embodiments, the reference value is a concentration of the element of fetal or embryonic origin in maternal serum of the same subject, and pregnancy failure is indicated when the ratio of the concentration of the element of fetal or embryonic origin in the vaginal fluid to the concentration of the element of fetal or embryonic origin in the maternal serum is greater than a predetermined threshold level.

In some embodiments, the predetermined threshold ratio level may be about 8, about 9, about 10, about 11, about 12, about 13, about 14, about 15 about 16, about 17, about 18, about 19, about 20, about 25, about 30.

In some such embodiments, wherein the element of fetal or embryonic origin is AFP, the predetermined threshold ratio level is about 13.4, such that pregnancy failure is indicated when the ratio of the concentration of AFP in vaginal fluid (such as vaginal blood) to the concentration of AFP in maternal serum of the same subject is greater than about 13.4.

In some embodiments, the reference value is a predetermined concentration value of the element of fetal or embryonic origin, such as a concentration value of from about 5 to about 20 ng/mL, such as, for example, about 5, about 6, about 7, about 8, about 9, about 10, about 11, about 12, about 12, about 14, about 15, about 16, about 17, about 18, about 19 or about 20 ng/ml, such that pregnancy failure is indicated when the concentration of the element of fetal or embryonic origin in vaginal fluid of the subject is greater than the predetermined concentration value. In some such embodiments, the element of fetal or embryonic origin is AFP. In some such embodiments, when the element of fetal or embryonic origin is AFP, the predetermined concentration value is from about 9 to about 10 ng/ml, preferably about 9.2 ng/m. In other such embodiments, the element of fetal or embryonic origin is an element other than AFP.

As used herein, the term "pregnancy failure" is intended to mean a non-viable pregnancy, including a failed intrauterine pregnancy; The terms 'miscarriage' and 'abortion' may also be used interchangeably to refer to a non-viable intrauterine pregnancy (IUP as above).

As used herein, the term "embryo" is intended to refer to a product of conception during the embryonic period. The embryonic period in defined as from conception until the end of 8 weeks gestation. As used herein, the term "fetus" is intended to refer to a product of conception during the fetal period. The fetal period is defined as beyond 8 weeks gestation. Abortion can occur during the embryonic or during the fetal periods, therefore, for simplification purposes, the terms "fetus' and "embryo" may also be used interchangeably.

In some embodiments, the pregnancy failure is a spontaneous abortion, which may be a complete abortion, an incomplete (partial) abortion or a missed abortion. In alternative embodiments, the pregnancy failure is an induced abortion.

In some embodiments, the pregnancy is a multiple pregnancy. In some such embodiments, the methods disclosed herein may identify the presence of at least one non-viable fetus or embryo, while one or more additional fetuses or embryos remain viable. In other such embodiments, all fetuses or embryos of the multiple pregnancy may be non-viable. In some embodiments, the multiple pregnancy is a heterotopic pregnancy (i.e. at least one intrauterine and at least one extra-uterine pregnancy occurring simultaneously). In some embodiments, all fetuses or embryos of the multiple pregnancy are intrauterine, and the concentration of the element of fetal or embryonic origin is proportional to the number of fetuses or embryos aborted, such that the ratio or concentration of the reference value is multiplied accordingly.

As used herein, the term "complete abortion" refers to an abortion in which all products of conception have been evacuated, including blood, tissue, embryo or fetus.

As used herein, the term "incomplete abortion" refers to an abortion in which bleeding has begun and the cervix is dilated, only some of the products of conception have been evacuated such that some fetal or embryonic tissue still remains in the uterus.

As used herein, the term "missed abortion" refers to an abortion in which the pregnancy is no longer viable, but no products of conception have been evacuated. The term "missed abortion" includes yolk sac miscarriage, embryonic miscarriage and fetal miscarriage, as defined by Kolte et el[5], which is incorporated by reference as if fully set out herein.

As used herein, the term "threatened abortion" refers to a condition in which vaginal bleeding of presumably uterine origin is identified, but in which a viable IUP is identified and no fetal or embryonic tissue has been passed.

In some embodiments, the pregnancy failure is a failure of a first or second trimester intrauterine pregnancy, i.e. a pregnancy prior to gestational week 28.

In some embodiments, the method disclosed herein is useful for identification of pregnancy failure in the absence of severe maternal hemorrhage.

The methods disclosed herein may also be useful in determining the location of a pregnancy, for example when an ectopic pregnancy is suspected.

According to some embodiments, the method disclosed herein may be used to identify an ectopic or molar pregnancy, which may be a continuing or terminated pregnancy (wherein the termination may be spontaneous or induced). In some such embodiments, the method further comprises determining a concentration of a hormonal marker of pregnancy, such as β-HCG, in the blood or urine of the subject and identifying the lack of a gestational sac within the uterus, such as by ultrasound scan. The presence of an ectopic or molar pregnancy is then identified when the level of a hormonal marker of pregnancy is above a predetermined threshold value, such as serum β-HCG of at least 1 mIU/mL, such that pregnancy is confirmed, but the ratio of a concentration of the element of fetal or embryonic origin, such as AFP, in the vaginal fluid to the concentration of the element of fetal or embryonic origin in the maternal serum is about 4.3 or less.

According to an aspect of some embodiments disclosed herein, there is provided a method for identifying a threatened abortion in a subject suffering from vaginal bleeding, the method comprising determining the source of bleeding; and determining a concentration of at least one element of fetal or embryonic origin in the vaginal fluid of the subject and comparing said concentration of said at least one element of fetal or embryonic origin to a reference value, wherein when said source of bleeding is uterine bleeding and said concentration of said at least one element of fetal or embryonic origin in said vaginal fluid is lower than said reference value. For example, in embodiments wherein the element of fetal or embryonic origin is AFP, the ratio of the concentration of AFP in vaginal blood to the concentration of AFP in maternal serum is less than 4.3. It should be noted that when vaginal bleeding is determined to originate from cervical bleeding, vaginal laceration, or other non-uterine sources, threatened abortion is not considered.

According to an aspect of some embodiments disclosed herein, there is provided a method for identifying and treating a pregnancy devoid of uterine fetal or embryonic tissue in a subject, the method comprising determining concentration of AFP in a specimen evacuated from the uterus of the subject; comparing the determined concentration of AFP to a reference value; wherein when the AFP concentration in the specimen evacuated from the uterus is below that of a reference value, absence of uterine fetal or embryonic tissue is indicated; and treating the subject in whom absence of uterine fetal or embryonic tissue is indicated by a procedure selected from the group consisting of pelvic surgery, cytotoxic therapy, dilation and curettage, aspiration of the uterine cavity, aspiration of the abdominal cavity, administration of uterotonics, administration of a progesterone antagonist, hysteroscopy, administration of intravenous fluid, injection of antibodies, administration of folic acid, administration of folinic acid, or combinations thereof.

According to some embodiments, the pregnancy has previously been confirmed by any method known in the art, such that confirmation of pregnancy does not constitute part of the method of the present invention.

According to some embodiments, the method further comprises confirming pregnancy in the subject, such as by determining the presence of a threshold concentration of human chorionic gonadotropin (hCG) in a specimen (fluid or solid) obtained from the subject. The threshold concentration of hCG may be a concentration of at least 1 mIU/ml in a bodily fluid of the subject (such as serum or urine) or a concentration of hCG of at least 1 mIU/mg in a solid tissue obtained from the subject (such as a fallopian tube). A concentration of least 1 mIU/mL in urine may be determined by obtaining a positive result in a standard, over-the-counter, commercial pregnancy test device. Determination using such a standard pregnancy test device may be performed by the patient.

Determination of the concentration of AFP may be performed using any method known in the art, for example by chemiluminescence immunoassay or a lateral flow immunoassay.

According to some embodiments, the reference value is 0.55 ng/mL. An AFP concentration in the specimen evacuated from the uterus may therefore be less than 0.55, less than about 0.5, less than about 0.45, less than about 0.4, less than about 0.35, less than about 0.3, less than about 0.25, less than about 0.2, less than about 0.15 or even less than about 0.1 ng/mL.

According to some embodiments, the specimen may be evacuated from the uterus by an active procedure, such as, for example, by dilation and curettage (D&C) or endometrial biopsy.

According to some embodiments, the specimen may be evacuated from the uterus by a passive process, such as bleeding or outflow from the uterus, which may exit the body of the subject via the vagina.

According to some embodiments, the specimen evacuated from the uterus is a liquid specimen (such as blood) or a solid tissue specimen.

According to some embodiments, the pregnancy devoid of uterine fetal or embryonic tissue is selected from the group consisting of an intrauterine anembryonic pregnancy, an ectopic pregnancy, a complete molar pregnancy and a complete miscarriage.

As used herein, the term "intrauterine anembryonic pregnancy" (also referred to as a blighted ovum) refers to a condition wherein a fertilized egg attaches to the uterine wall and a pregnancy sac is formed, but the embryo does not develop.

As used herein, the term "ectopic pregnancy" refers to a condition wherein a fertilized egg implants outside the uterus.

As used herein, the term "molar pregnancy" refers to a condition wherein an abnormally fertilized egg implants in the uterus. This abnormally fertilized egg can form a 'complete' or 'partial' mole. Both are abnormal pregnancies. The complete mole is an abnormal placental tissue which is devoid of embryonic or fetal tissue.

According to some embodiments, the specimen evacuated from the uterus is collected on an absorbent material, such as cotton, a feminine hygienic pad, a tampon, or an item of underwear.

According to some embodiments, the absorbent material is provided within a feminine hygiene pad.

According to some embodiments, the method further comprises isolating a portion of the absorbent material containing the specimen evacuated from the uterus; extracting the specimen from the portion of absorbent material in a solvent; wherein the concentration of AFP is determined in the solvent. Non-limiting examples of suitable solvents include water based solutions such as saline, water for injection, Hartman's solution. Other solutions may include alcohol, acetone, a detergent, or oil or combinations thereof.

According to some embodiments, isolating a portion of the absorbent material comprises cutting an area of material from the absorbent material, such as the feminine hygiene pad, for example in the form of a patch and the concentration of AFP in the patch is determined.

According to some such embodiments, the method further comprises obtaining a sample of maternal serum of the patient, determining a concentration of thyroid stimulating hormone (TSH) in the maternal serum [TSHms]; determining a concentration of TSH in the specimen evacuated from the uterus (i.e., TSH in the vaginal blood, [TSHvb]); calculating a dilution factor [DF] wherein DF=TSHms/TSHvb; and calculating an original concentration of AFP in said specimen evacuated from the uterus prior to dilution in the solvent wherein the original concentration of AFP=concentration of AFP determined in said solvent×DF.

The quantification of creatinine can serve is an alternative for TSH quantification in maternal serum and/or vaginal fluid.

A non-limiting example of a situation in which any of the methods disclosed herein may be useful for identification of an ectopic pregnancy or other abnormal pregnancy (such as molar pregnancy or blighted ovum) is one in which a woman in whom pregnancy has previously been determined, based on the concentration of a hormonal marker of pregnancy, such as β-HCG, in serum or urine (e.g. serum β-HCG concentration of 10,000 mIU/mL) but no conclusive sonographic findings (such that the pregnancy is of unknown location), experiences first trimester bleeding. The inconclusive sonographic findings may be due to a failure of an IUP with intrauterine gestational sac that cannot be distinguished from the surrounding tissue or, alternatively, may be due to an ectopic pregnancy not visualized by ultrasound scan).

In such a case, if the ratio of $[AFP]_{vaginal\ blood}/[AFP]_{maternal\ serum}$ is above 13.4, failure of an IUP is indicated. However, if the ratio of $[AFP]_{vaginal\ blood}/[AFP]_{maternal\ serum}$ is 4.3 or less, the pregnancy might be an ectopic pregnancy, a blighted ovum, or a complete mole (such that no intrauterine embryonic/fetal tissue is present). In the case of a molar pregnancy, since a complete mole does not contain embryonic/fetal tissue, the absolute concentrations of AFP are very low i.e. less than about 20 ng/mL.

Similarly, in such a case if the concentration of AFP in blood evacuated passively from the uterus via the vagina is less than 0.55 ng/mL, the pregnancy might be an ectopic pregnancy, a blighted ovum, a complete mole, or a complete miscarriage.

According to an aspect of some embodiments of the present invention, there is provided a method for identifying and treating a presence of fetal or embryonic tissue in a location of a subject other than the uterus, the method comprising determining a concentration of AFP in a non-uterine specimen obtained from the subject; comparing the concentration of AFP in the specimen to a reference value; wherein when the AFP concentration in the specimen is above that of a reference value, presence of embryonic or fetal tissue is indicated in the obtained specimen and treating the subject in whom presence of uterine fetal or embryonic tissue is indicated by a procedure selected from the group consisting of pelvic surgery, cytotoxic therapy, dilation and curettage, aspiration of the uterine cavity, administration of uterotonics, administration of a progesterone antagonist, hysteroscopy, administration of intravenous fluid, injection of antibodies, administration of folic acid, administration of folinic acid, or combinations thereof.

According to some embodiments, the reference value is 0.5 ng/mL. Hence, presence of fetal or embryonic tissue is indicated in the obtained specimen when the AFP concentration in the specimen is above 0.5 ng/mL, such as, for example, above 0.5, above about 1.0, above about 1.5, above about 2.0, above about 2.5, above about 3.0, above about 3.5, above about 4.0, above about 4.5, above about 5.0, above about 5.5, above about 6.0, above about 6.5, above about 7.0, above about 7.5, above about 8.0, above about 8.5, above about 9.0, above about 9.5 or even above about 10.0 ng/mL.

According to an aspect of some embodiments of the present invention, there is provided a method for identifying and treating an absence of fetal or embryonic tissue in a pregnant subject, the method comprising determining a concentration of AFP in a specimen obtained from the subject; comparing the concentration of AFP to a reference value; wherein when the AFP concentration in the specimen obtained from a subject is below that of a reference value, absence of fetal or embryonic tissue is indicated in the obtained specimen; and treating the subject in whom absence of uterine fetal or embryonic tissue is indicated by a procedure selected from the group consisting of pelvic surgery, cytotoxic therapy, dilation and curettage, aspiration of the uterine cavity, aspiration of abdominal cavity, administration of uterotonics, administration of a progesterone antagonist, hysteroscopy, administration of intravenous fluid, injection of antibodies, administration of folic acid, administration of folinic acid, or combinations thereof.

According to some embodiments, the reference value is 0.5 ng/mL. Hence, absence of fetal or embryonic tissue is indicated in the obtained specimen when the AFP concentration in the specimen is below 0.5 ng/mL.

According to an aspect of some embodiments of the present invention, there is provided a method for identifying and treating pregnancy failure in a subject, the method comprising: determining a concentration of fetal hemoglobin (HbF) in the vaginal fluid of the subject; and comparing the concentration of said HbF to a reference value, wherein when the concentration of HbF in the vaginal fluid is higher than the reference value, pregnancy failure is indicated; and treating the subject in whom pregnancy failure is indicated by a procedure selected from the group consisting of pelvic surgery, cytotoxic therapy, dilation and curettage, aspiration of the uterine cavity, administration of uterotonics, aspiration of the abdominal cavity, administration of a progester-one antagonist, hysteroscopy, administration of intravenous fluid, injection of antibodies, administration of folic acid, administration of folinic acid, or combinations thereof.

According to an aspect of some embodiments of the present invention, there is provided a method for identifying and treating an intrauterine pregnancy in a subject, the method comprising: determining a level of fetal hemoglobin (HbF) in a specimen evacuated from the uterus of the subject; and comparing the concentration of HbF to a reference value, wherein when the concentration of HbF in the specimen is higher than the reference value, intrauterine pregnancy is indicated; and treating the subject in whom intrauterine pregnancy is indicated by a procedure selected from the group consisting of pelvic surgery, cytotoxic therapy, dilation and curettage, aspiration of the uterine cavity, administration of uterotonics, aspiration of the abdominal cavity, administration of a progesterone antagonist, hysteroscopy, administration of intravenous fluid, injection of antibodies, administration of folic acid, administration of folinic acid, or combinations thereof.

Unless otherwise defined, all technical and scientific terms used herein have the same meaning as commonly understood by one of ordinary skill in the art to which the invention pertains. In addition, the descriptions, materials, methods, and examples are illustrative only and not intended to be limiting. Methods and materials similar or equivalent to those described herein can be used in the practices of the present invention.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10% of that value.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1:
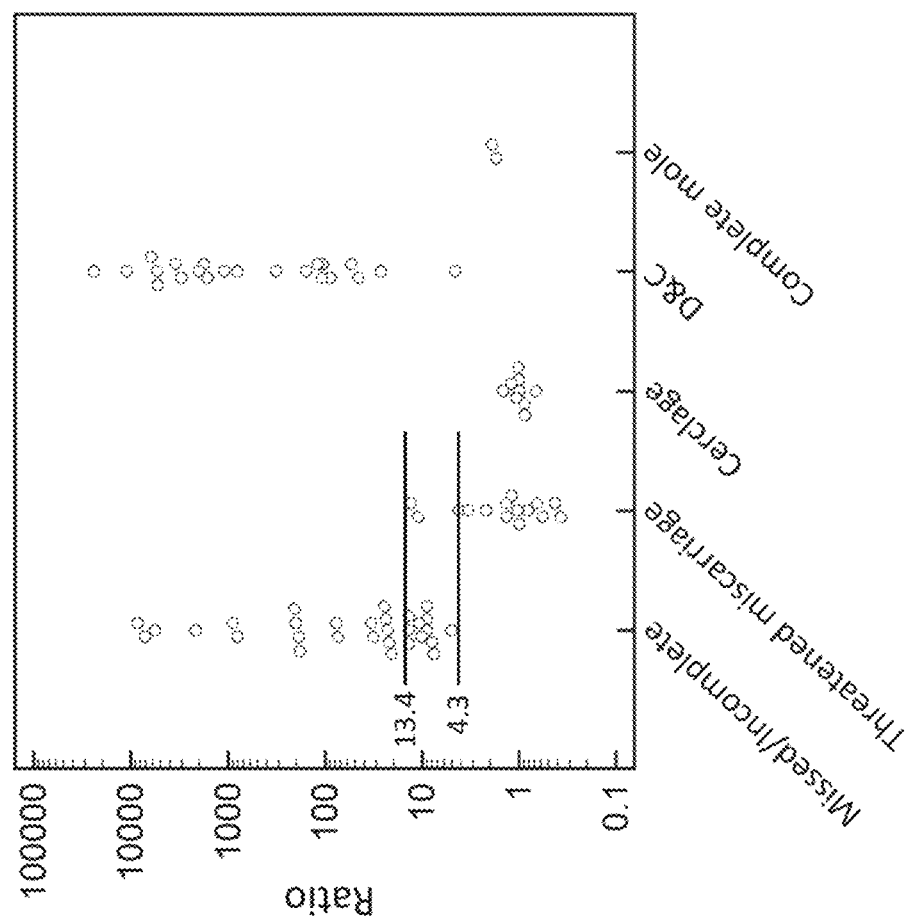
FIG. 1 is a dot graph showing alpha-fetoprotein (AFP) concentration ratio distributions for four subject groups (missed/incomplete abortion (group 1), threatened abortion (group 2), cerclage (group 3), D&C (group 4); as well as for two subjects with a complete molar pregnancy. Each dot represents the ratio $[AFP]_{vaginal\ blood}/[AFP]_{maternal\ serum}$ or $[AFP]_{POC}/[AFP]_{maternal\ serum}$ in a single subject.

The invention, in some embodiments thereof, relates to a method for identification of pregnancy failure comprising comparing a concentration of at least one element of fetal or embryonic origin in the vaginal fluid of a subject to a reference concentration of the same element of fetal or embryonic origin.

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. The phraseology and terminology employed herein are for descriptive purpose and should not be regarded as limiting.

EXAMPLES

Example 1

AFP Concentration as an Indicator of Pregnancy Failure

Materials and Methods:

Subjects

A total of 78 pregnant women in their first or second trimesters were recruited at the Maimonides Medical Center Labor and Delivery Department, Brooklyn, N.Y.

Written consent was obtained from all study participants prior to participation.

Four subject groups were evaluated:
(1) Women with incomplete/missed abortion experiencing vaginal bleeding as identified according to the diagnostic criteria for a nonviable intrauterine pregnancy (IUP) provided by Doubilet et al.[3], which is incorporated by reference as if fully set forth herein;
(2) Women with threatened abortion i.e. not passing fetal or embryonic tissue, experiencing vaginal bleeding, with a confirmed IUP and visible fetal or embryonic heartbeat;
(3) Women experiencing vaginal bleeding during cerclage placement, with visible fetal or embryonic heartbeat before and after the cerclage procedure (negative control group for passage of fetal or embryonic tissue into the vagina); and
(4) Women undergoing dilation and curettage (D&C) and having confirmed IUP (positive control group for presence of fetal or embryonic tissue).

After recruitment and initial evaluation (that included history taking, physical examination, sonographic imaging, and laboratory testing), each subject was assigned to one of the four groups described above; 31, 15, 9, and 23 women were assigned to Groups (1) to (4), respectively. For subjects in Group (3), McDonald (n=4) or Modified Shirodkar (n=5) techniques were used.

Confirmation of IUP

Specimens of tissue were obtained from the vagina for subjects in Group (1) and from the uterus (products of conception, POC) from subjects in Group (4). IUP was confirmed by a histopathological review of the tissue specimens. All fetal or embryonic tissue was subsequently evacuated from subjects in Group (1), either spontaneously or actively with the aid of uterotonics, with or without a D&C.

IUP was confirmed by sonogram for subjects in Groups (2) and (3), and no solid tissue specimens were obtained from subjects in these groups.

Subjects already recruited to Groups (1) and (4) were excluded from analysis if the histopatological report did not confirm the presence of intrauterine embryonic/fetal tissue.

Measurement of AFP Concentrations

AFP concentrations were measured by a fully automated assay (a chemiluminescence immunoassay by Beckman Coulter Inc., USA; Cat. No. 33211).

For each subject group, AFP concentration in the vaginal blood (Groups (1) to (3)) or in the liquid component of the evacuated POC (Group (4)) was compared to the AFP concentration in the maternal serum of the same subject. Values were expressed as the median with the corresponding ranges. Wilcoxon signed-rank test was used for paired samples.

Concentration ratios were calculated for each subject individually as follows: $[AFP]_{vaginal\ blood}/[AFP]_{maternal\ serum}$ (for subjects in Groups (1) to (3)); $[AFP]_{POC}/[AFP]_{maternal\ serum}$ (for subjects in Group (4)). Receiver operating characteristic (ROC) analysis for the detection of fetal or embryonic tissue in the vaginal blood according to AFP concentration ratios was performed (Group (1) vs. Group (2)).

It was assumed by the present Inventor that AFP concentration in the fetal or embryonic serum is at least 1,000 times higher than in the maternal serum[2]. Since this resulted in an extremely large difference and tiny sample size, the present Inventor chose to limit the effect size to 0.8 resulting in 12 patients per group for 80% power, with alpha=0.05 (online sample size calculator: https://www.anzmtg.org/stats). Statistical data were analyzed and graphical illustrations were constructed using MedCalc software (MedCalc Software bvba, Ostend, Belgium).

Results for this embodiment are presented in Table 1 below and in FIGS. 1 and 2.

Results

Confirmation of IUP

Except for two women, all histopathological reports retrospectively confirmed the presence of an IUP with embryonic/fetal tissue in subjects from Groups (1) and (4). One subject who was initially assigned to Group (1), and later had a D&C, and one woman who was initially scheduled for D&C for "an abnormal pregnancy" and assigned to Group (4), had histopathological reports showing complete moles (i.e. no embryonic/fetal tissue). These two cases were excluded from the original group assignments but the AFP concentrations were measured in the maternal sera and in the obtained intrauterine specimens and are presented in FIG. 1 below.

Fetal or embryonic heartbeats were identified for all subjects assigned to Group (3), both pre- and post-cerclage procedure, and none ruptured their membranes in conjunction with the procedure. Therefore, no subjects originally assigned to Groups (2) and (3) were subsequently excluded.

AFP Concentrations

Table 1 below present alpha-fetoprotein (AFP) concentration ratio distributions for Groups (1) to (4). In FIG. 1, each dot represents the ratio $[AFP]_{vaginal\ blood}/[AFP]_{maternal\ serum}$ or $[AFP]_{POC}/[AFP]_{maternal\ serum}$ in a single subject. In FIG. 1 the four groups are represented as well as the two subjects with a complete molar pregnancy.

TABLE 1

| Group no. | Gestational age range (weeks) | Median $[AFP]_{vaginal\ blood}$ (ng/mL) or Median $[AFP]_{POC}$ (ng/mL; D&C group only)[a] | Median $[AFP]_{maternal\ serum}$ (ng/mL) | p | Median ratio[b] |
|---|---|---|---|---|---|
| 1 (n = 30) | 7 to 15 | 192.2 (9.2 to 195,242) | 6.2 (0.9 to 211) | <0.001 | 24.5 (5.1 to 8,620) |
| 2 (n = 15) | 6 to 22 | 109 (1.8 to 712) | 73.1 (1.5 to 280) | 0.389 | 1.2 (0.4 to 13.4) |
| 3 (n = 9) | 14 to 22 | 26.0 (14.8 to 108) | 25.2 (18.7 to 73.3) | 1 | 1.01 (0.7 to 1.5) |
| 4 (n = 22) | 5 to 20 | 16,783 (122 to 155,466) | 18.3 (0.9 to 755) | <0.001 | 957 (4.6 to 24,216) |

As presented in Table 1, AFP concentrations in vaginal blood (Group (1) and in POC (Group (4) were significantly higher than AFP concentration in the maternal serum in all subjects (Table 1).

Specifically, for Group (1), the median AFP concentration was 192.2 ng/mL in the vaginal blood and 6.2 ng/mL in the maternal serum (p<0.001). The median ratio was 24.5 with a range of 5.1 to 8,620 (Table 1).

For Group (4), the median AFP was 16,783 ng/mL in the liquid component of the POC and 18.3 ng/mL in the maternal serum (p<0.001). The median ratio was 957 with a range of 4.6 to 24,216 (Table 1).

For Groups (3) and (4), the median AFP concentration in the vaginal blood was relatively low and did not differ significantly from the median concentration in the maternal serum (Table 1).

The ratio distribution for each group is presented in FIG. 1.

As seen in Table 1 and FIG. 1, the median concentration ratio of AFP in vaginal blood to AFP in maternal serum was 24.5 (5.1-8,620) for group (1) (n=30), whereas they were only 1.2 (0.4-13.4) and 1.01 (0.7-1.5) for group (2) (n=15) and group (3) (n=9), respectively. Median concentration ratio of AFP in POC for group (4) (n=22) was 957 (4.6-24, 216).

Figure 2:
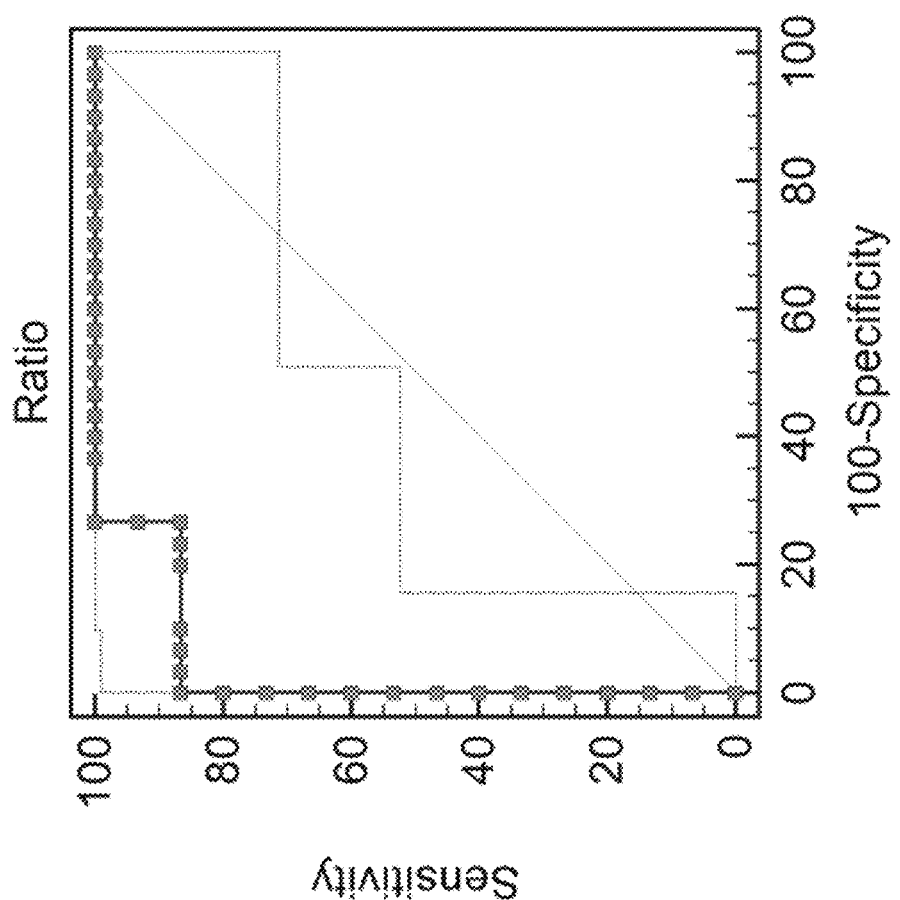
FIG. 2 is a graph showing receiver operating characteristic (ROC) analysis for subject groups (1) and (2) as defined in FIG. 1.

Receiver operating characteristic analyses (ROC) of Groups (1) and (2) are presented in FIG. 2. The determined cutoff levels for AFP concentration ratios was 4.3, for which the corresponding sensitivity was 100% (confidence interval [CI] 88.4-100%) and the corresponding specificity was 86.7% (CI 59.5-98.3%). The calculated area under the curve was 0.96 (CI 0.86-1.0).

Raising the cutoff ratio to 13.4 resulted in a 73.3% sensitivity for 100% specificity (FIG. 1).

A ratio of 4.3 or lower was thus found to be consistent with a threatened abortion, whereas a ratio of above 13.4 was found to be consistent with pregnancy failure.

As further seen in Table 1, for the two subjects initially assigned to Groups (1) and (4), respectively, but later found to have complete moles, the AFP concentration in vaginal blood was 2.3 ng/mL (for the subject assigned to Group (1)) and in the liquid component of the POC was 1.9 ng/mL (for the subject assigned to Group (4)), and the AFP concentrations in the maternal sera of the two subjects were 1.2 and 1.1 ng/mL, respectively. Each of these values was thus very low for the two subjects, and was within the respective ranges for non-pregnant women. The AFP concentration ratios were 1.92 and 1.73, respectively (AFP ratios for these two subjects are represented in FIG. 1).

Conclusion

The present Inventor have surprisingly found that a ratio of $[AFP]_{vaginal\ blood}/[AFP]_{maternal\ serum}$ of 4.3 or lower is consistent with a threatened abortion in subjects suffering from bleeding of intrauterine origin, whereas a ratio of above 13.4 is consistent with pregnancy failure. A ratio that falls between 4.3 and 13.4 (including 13.4) should be interpreted as indeterminate.

It should be noted that the given values are those for AFP. Different indicators of pregnancy failure may be used, and may involve different concentration ratios.

The present Inventor thus disclose a novel approach for the diagnosis of pregnancy failure based on the passage of fetal or embryonic tissue, by quantification of AFP concentration in the vaginal blood of a subject. Excluding the relatively rare possibilities of multiple or heterotopic pregnancies, an $[AFP]_{vaginal\ blood}/[AFP]_{maternal\ serum}$ ratio above 13.4 is shown to indicate pregnancy failure. It is further considered that the higher the ratio, the higher the possibility of a pregnancy failure.

A limitation of this approach would be its reliability in the setting of severe maternal hemorrhage. Heavy bleeding could greatly dilute the AFP originating from the fetal or embryonic tissue and lead to a false negative result (i.e., a low ratio). Therefore, in cases of maternal hemorrhage, this technique should be used with caution or not used at all.

The Inventor conclude that sampling vaginal blood in the setting of first trimester (or early second trimester) bleeding or sampling the liquid component of POC following a diagnostic or a therapeutic D&C can serve as a confirmation of a dissolved/mixed fetal or embryonic tissue in the obtained specimen. A strength of this approach is that it is a same-day (in some cases, a result is available within 25-30 minutes from the time it is received in the lab), simple test that has the potential to provide a reliable diagnosis of an IUP failure.

Example 2

DNA Concentration as an Indicator of Pregnancy Failure

An additional example of an element of fetal or embryonic origin for use in the methods of the present invention is fetal or embryonic DNA/RNA. The presence of fetal or embryonic genetic material above a threshold level of about 2% of the total DNA/RNA sample obtained can confirm, for example, pregnancy failure. Moreover, laboratory or bedside tests for the sequence of these molecules can provide information about the etiology of the pregnancy failure (e.g., fetal or embryonic chromosomal abnormalities) without or prior to obtaining fetal or embryonic tissue. For example, trisomy 13 and 18 are not rare and can result in early pregnancy loss. The sample of vaginal bleeding for these genetic abnormalities or other abnormalities such as mutations, deletions, duplications, and oligonucleotide repeats can provide the etiology of the failing pregnancy.

DNA/RNA levels may be detected by any method known in the art. As a non-limiting example, a bedside test for DNA detection can be done with a lateral flow assay employing DNA biorecognition molecules such as aptamers or molecular beacons[4] as disclosed by Sajid M et al., which is incorporated by reference as if fully set out herein. For example, the biorecognition molecules can bind specific DNA/RNA sequences which are associated with known mutations/excess repeats as well as abnormal sequences following deletions or additions of genetic material. Therefore, a lateral flow assay employing biorecognition molecules can be a powerful tool for detecting fetal or embryonic DNA/RNA and recognizing sequence abnormalities almost in or in real time (i.e., while vaginal bleeding occurs).

Subjects are recruited, evaluated, and an IUP confirmed as described for Example 1 above.

DNA concentration is measured by lateral flow assay.

For each subject group, DNA concentration in the vaginal blood (Groups (1) to (3)) or in the liquid component of the evacuated POC (Group (4)) is compared to the DNA concentration in the maternal serum of the same subject. Values are expressed as the median with the corresponding ranges. Wilcoxon signed-rank test is used for paired samples.

Concentration ratios are calculated for each subject individually as follows: $[DNA]_{vaginal\ blood}/[DNA]_{maternal\ serum}$ (for subjects in Groups (1) to (3)); $[DNA]_{POC}/[DNA]_{maternal\ serum}$ (for subjects in Group (4)). Receiver operating characteristic (ROC) analysis for the detection of fetal or embryonic tissue in the vaginal blood according to DNA concentration ratios is performed (Group (1) vs. Group (2)).

Statistical data are analyzed and graphical illustrations are constructed using MedCalc software (MedCalc Software bvba, Ostend, Belgium).

Example 3

Fetal/Embryonal Hemoglobin Concentration as an Indicator of Pregnancy Failure An additional example of an element of fetal or embryonic origin for use in the methods of the present invention is fetal or embryonic hemoglobin (HbF). The presence of fetal or embryonic hemoglobin above a threshold level detected in the maternal serum can confirm pregnancy failure. Alternatively, since oftentimes HbF is not detected at all in the maternal serum or is present in relatively low levels, a detectable HbF in the vaginal blood above a determined threshold can confirm pregnancy failure, such that the threshold level is zero or a relatively low number/percentage. In general, HbF in the newborn is 60 to 80% of the total hemoglobin whereas it is only 0 to 2% in the maternal serum.

Subjects were recruited, evaluated, and an IUP confirmed as described for Example 1 above.

Fetal or embryonic hemoglobin concentration was measured using an immunoassay using antibodies reacting specifically with human hemoglobin F (Anti-fetal hemoglobin antibody ab19364, Abcam, Cambridge, UK).

Figure 3:
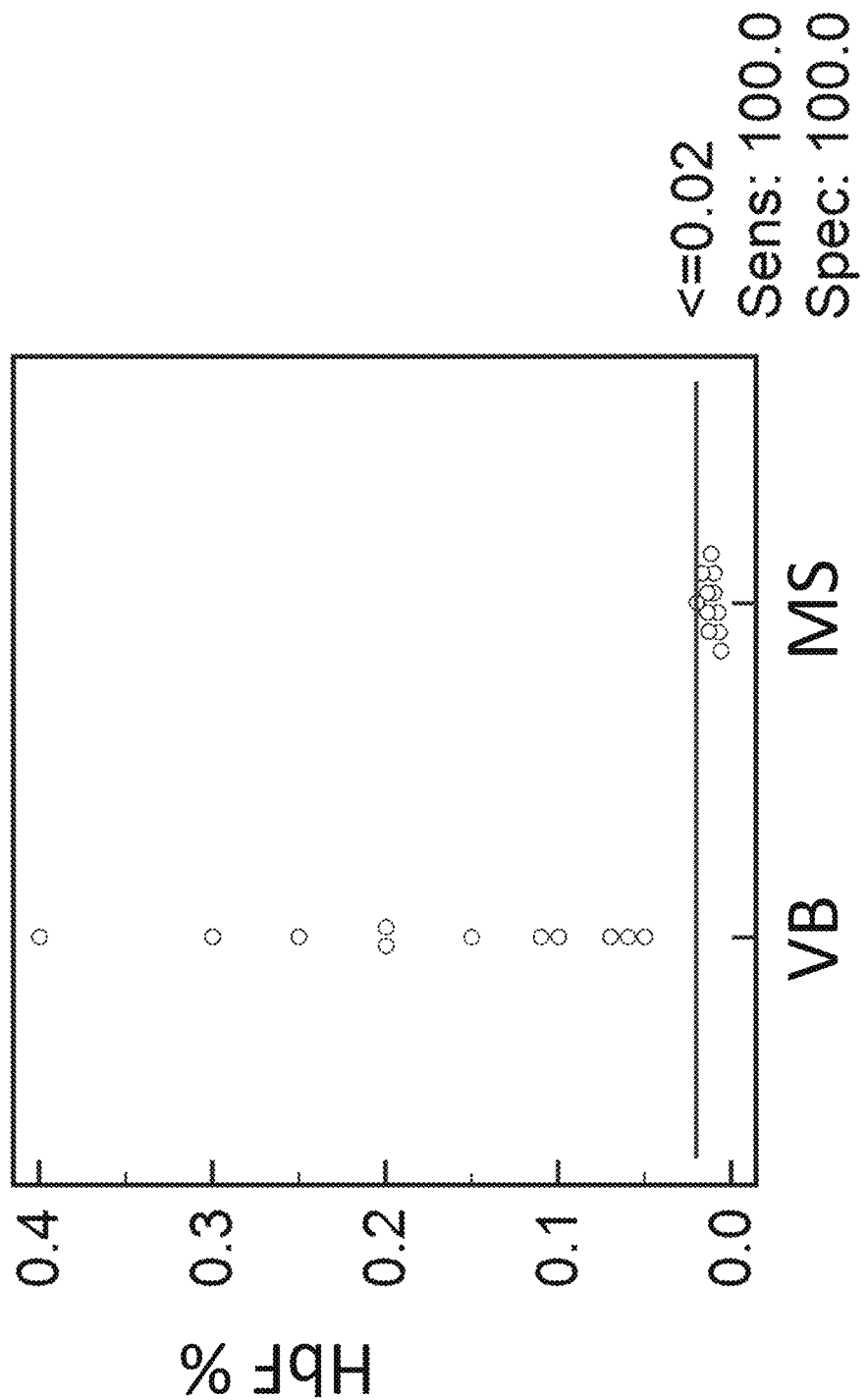
FIG. 3 is a dot graph showing fetal hemoglobin (HbF) percentage in vaginal blood (VB) and in maternal serum (MS). Each dot represents the fraction (%) of HbF of the total hemoglobin detected in the sample.
Figure 4:
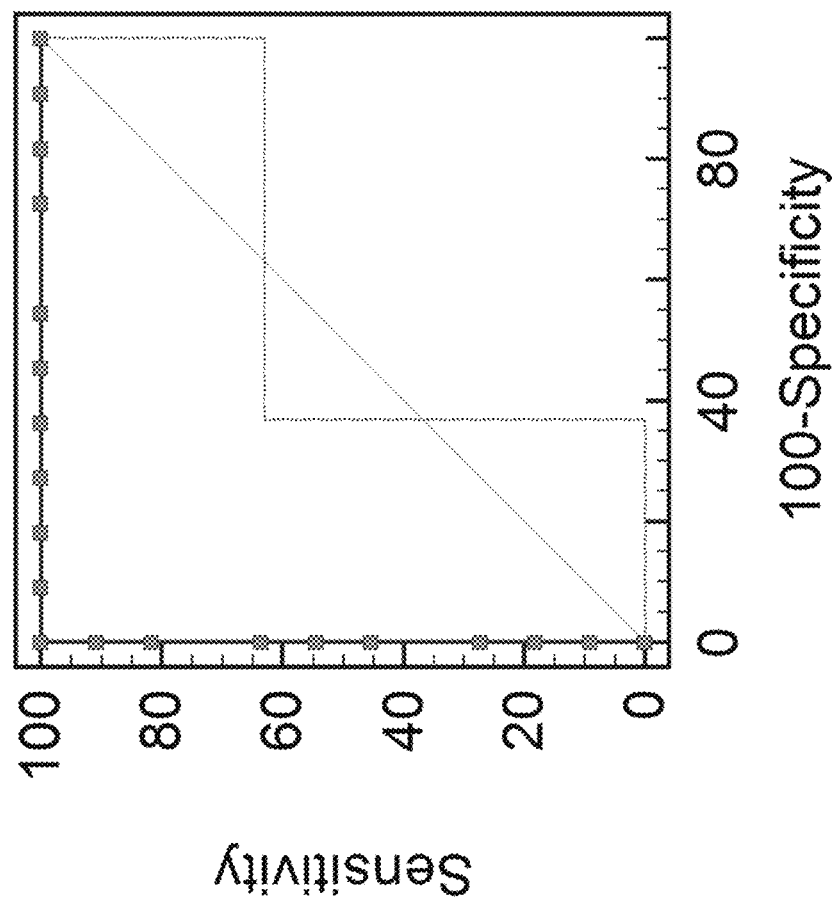
FIG. 4 is a graph showing ROC analyses of fetal hemoglobin fraction in the vaginal blood vs. its fraction in the maternal serum. The predetermined threshold is 0.02 (2%).

HbF percentage of the total hemoglobin in the sample was calculated for each subject individually as follows: HbF % in the vaginal blood and HbF % in the maternal serum (FIG. 3). Receiver operating characteristic (ROC) analysis for the detection of fetal tissue in the vaginal blood according to hemoglobin concentrations was performed (FIG. 4). Statistical data were analyzed and graphical illustrations were constructed using MedCalc software (MedCalc Software bvba, Ostend, Belgium).

Example 4

Prediction of Pregnancy Location and Outcome in Women with First Trimester Bleeding by the Detection of Alpha-Fetoprotein (AFP) in Vaginal Blood Background:

The aim of the present study was to detect the presence of AFP in specimens evacuated from the uterus and to relate the detected AFP concentrations to a condition of pregnancy, such as the location of pregnancy.

The specimens comprised blood evacuated spontaneously from the uterus via the vagina and collected on feminine hygiene pads from women with $1^{st}$ or $2^{nd}$ trimester bleeding.

As is known in the art[2], at any given gestational age, AFP concentration is at least 1,000 times higher in the fetal serum in comparison to its concentration in the maternal serum.

The present inventors assumed that in the early stages of pregnancy, TSH is produced by the mother only whereas AFP is produced by the embryo/fetus only. Vaginal blood can contain components which originate from both the mother and the embryo/fetus or from the mother alone. Vaginal blood is unlikely to contain components which originate from the fetus alone. Therefore, vaginal blood containing mostly embryonic/fetal tissue should contain a high level of AFP and a low level of TSH.

Figure 5:
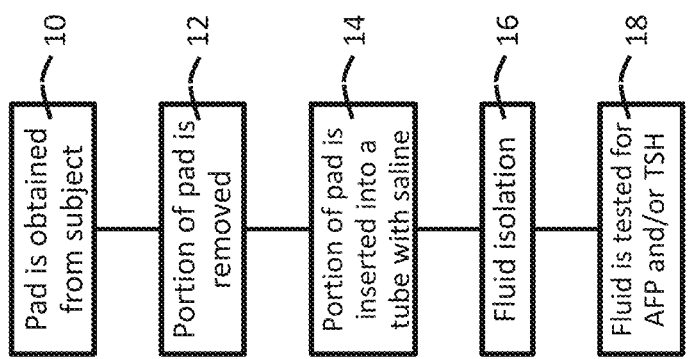
FIG. 5 is a flow chart depicting an exemplary method for processing a specimen evacuated from the uterus of a subject in accordance with the principles of the present invention.

A flow chart depicting an embodiment of a method for processing a specimen evacuated from the uterus of a subject is shown in FIG. 5. In this embodiment, the specimen to be processed is evacuated passively from the uterus of the subject via vaginal blood and collected on a feminine hygienic pad.

The pad is obtained from the subject (step 10) when vaginal blood can be detected on the pad by visual inspection with the naked eye. A portion of the pad containing vaginal blood is removed (step 12), for example by cutting a portion containing the blood from the pad. The portion of the pad is then inserted into a receptacle (such as a test tube) containing a solvent such as saline (step 14). The vaginal blood is isolated from the portion of the pad (step 16); and the concentration of AFP in the isolated vaginal blood is determined (step 18).

Materials and Methods:

Subjects 56 pregnant women with vaginal bleeding at any gestational age who were evaluated for pregnancy viability at a medical center. Patient recruitment was conducted on-site during the evaluation for pregnancy viability.

The following information was obtained for each patient: Age, race, BMI (to identify normal weight, overweight and obese subjects), medical and surgical history, medications used, including recent use of reproductive hormones, reason for and type of currently scheduled surgery, smoking status, pathological surgical findings from any recent surgery.

Written consent was obtained from all study participants prior to participation.

Venous blood specimens were collected into a designated chemistry tube and sent AFP, TSH, and progesterone quantification.

Vaginal blood specimens were collected using feminine hygienic pads previously worn by the subject in which blood spotting was visible to the naked eye. As a control group, AFP and TSH concentrations were quantified from blood collected on pads that were in contact with an IUP actively evacuated from the uterus (after a D&C). The women in this group did not necessarily have vaginal bleeding during their pregnancy The specimens were sent to the medical center's chemistry lab for AFP, TSH, and progesterone quantification. Additionally, for which dilation and curettage (D&C) was performed, evacuated tissue was sent for pathological examination.

Processing and Analysis of Vaginal Blood Specimens

1×1 cm$^2$ patches with vaginal blood were removed from the previously worn feminine hygienic pad and placed into a tube containing 1 mL saline. A filter sampler (a plunger with a filter; Porex, Atlanta, Ga., USA) was used to compress the pad patch in the tube and extract and isolate the liquid component out of the patch. This procedure enabled AFP and TSH quantification in these reconstituted vaginal blood specimens.

The dissolved AFP and TSH contained in the vaginal blood (AFPvb and TSHvb, respectively) were quantified by an automatic chemiluminescence assay (Cobas e411 analyser, Roche, Germany). Additionally, AFP lateral flow immunoassay strips were dipped into those tubes containing the isolated vaginal fluid specimens. The qualitative results of the AFP strips were read 5-10 minutes after dipping. Those AFP strips are positive for AFP concentrations of 20-30 ng/mL or higher. Alternatively, AFP strips were embedded in hygienic pads and therefore were in direct or close contact with the vaginal fluid. This approach did not require removing pad patches. In both approaches, the lateral flow capillary action was initiated upon fluid contact with the strip.

Processing and Analysis of Solid Tissue

Hematoxylin and eosin (H&E) stained histopathology slides were examined using standard histopathologic criteria for pregnancy loss examination. These included examinations for the presence of embryonic/fetal tissue, acute inflammation, immunologic rejection, increased thrombus formation and any dysmorphic features of the chorionic villi which are indicative of genetic or developmental abnormalities in the pregnancy. The histopathological results were correlated with AFPvb/AFPms ratios.

Definitions:

Regarding the same pregnant patient, two samples were obtained—vaginal blood collected in a pad and maternal serum. TSH and AFP were quantified AFP in vaginal blood (AFPvb) was collected in a pad and quantified in the tube containing 1 mL saline (details above).

TSH in vaginal blood (TSHvb) was collected in a pad and quantified in the tube containing 1 mL saline (details above).

AFP in maternal serum (AFPms)

TSH in maternal serum (TSHms)

Algorithm

The original concentration of AFPvb in the specimen (before dilution with solvent) was calculated as follows:

Step 1—Dilution factor (DF)=[TSHms]/[TSHvb]

Step 2—original AFPvb (before dilution)=[AFPvb]×DF

Step 3—The original AFP concentration in vaginal blood (original AFPvb) was compared to the AFP concentration in the maternal serum (AFPms) of the same subject, at the time of presentation with vaginal bleeding. Follow up was conducted for all subjects until a final diagnosis was established (e.g., threatened, missed, complete or incomplete miscarriage; extrauterine, molar, and anembryonic pregnancies).

Patients were tested for evidence of passage of tissue and pelvic US was carried out on the day of specimen collection.

For each participant one of the following outcomes was determined:

1. Clinical and/or histopathologic evidence of passage of intrauterine embryonic/fetal tissue (a failed intrauterine pregnancy (IUP)).
2. A threatened miscarriage with subsequent ongoing clinical pregnancy (heartbeat documented on ultrasound on the day of pad collection or at least once within the subsequent 5 weeks).
3. A complete miscarriage.
4. An ectopic pregnancy.

As a control group, AFP concentration was quantified from blood collected on pads that were in contact with an IUP actively evacuated from the uterus (after a D&C). These pads absorbed at least 0.5 mL of fluid (estimation by visual inspection). The women in this group did not necessarily have vaginal bleeding during their pregnancy. 1×1 cm$^2$ patches with vaginal blood were removed from the pad and placed into a tube containing 1 mL saline.

The following questions were addressed:

Is low original AFPvb/AFPms ratio consistent with a threatened miscarriage?

Is low original AFPvb/AFPms ratio consistent with a complete mole?

Is low original AFPvb/AFPms ratio consistent with an anembryonic pregnancy?

Is low original AFPvb/AFPms ratio consistent with an ectopic pregnancy?

Is low original AFPvb/AFPms ratio consistent with a complete miscarriage?

Is high original AFPvb/AFPms ratio consistent with a missed miscarriage?

Is high original AFPvb/AFPms ratio consistent with an incomplete miscarriage?

Is high original AFPvb/AFPms ratio consistent with rupture of membranes in early pregnancy?

Is high original AFPvb/AFPms ratio consistent with specific pathologic features identified upon histologic examination of the loss material?

Is high original AFPvb/AFPms, consistent with a passage of fetal tissue?
Is just a detection of AFPvb (without the calculation of original AFPvb) consistent with passage of embryonic/fetal tissue?
Is a positive result, using a lateral flow immunoassay AFP embedded in a pad, consistent with passage of embryonic/fetal tissue?

Results:

The data for each recruited patient are represented in Table 2.

Figure 6:
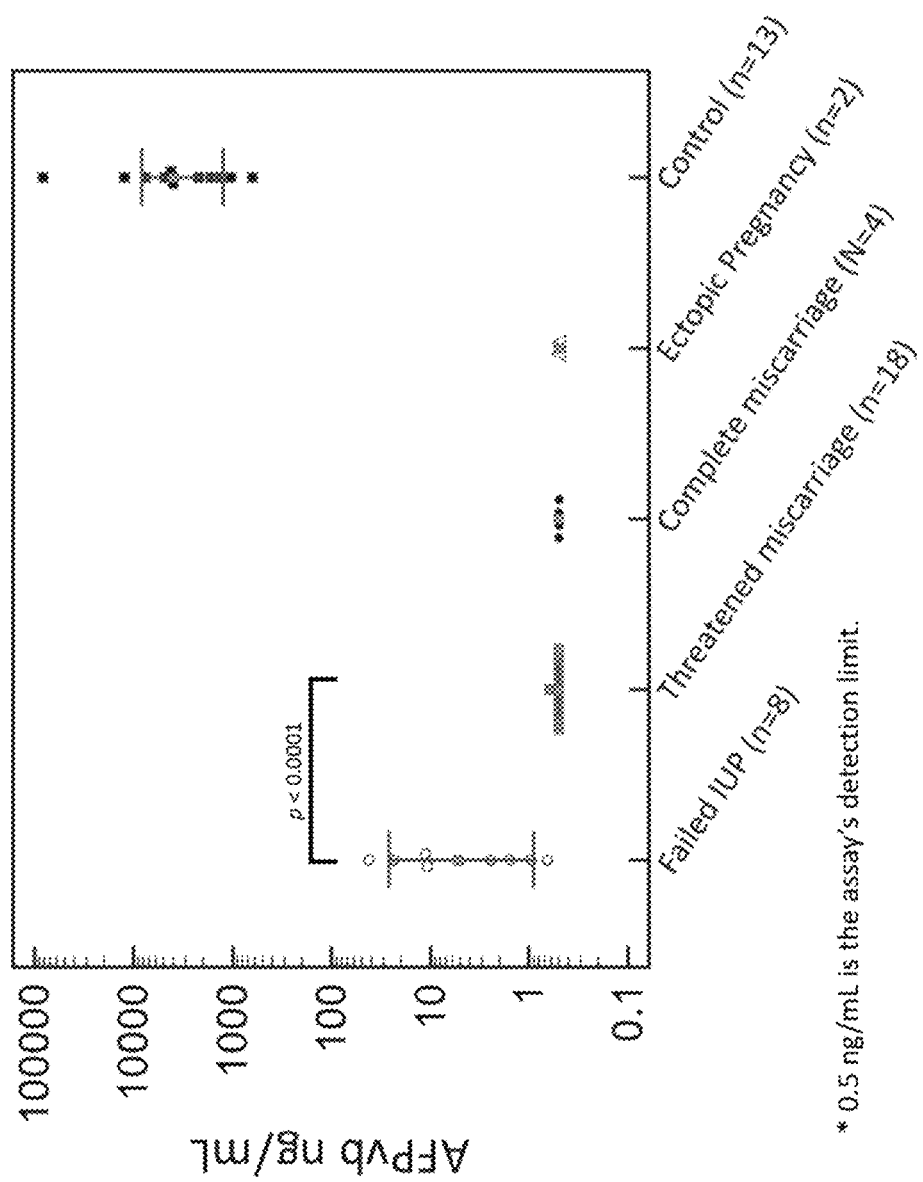
FIG. 6 is a graph representing absolute AFP concentrations after extracting blood from pads, gauzes, or other absorbent materials.

The results of the quantitative automatic test and the correlation to an identified outcome are presented in FIG. 6 (for a portion of the recruited patients). Of note, these calculations were not adjusted for dilution factor (DFs) calculated according to TSHms and TSHvb.

TABLE 2

| Estimated bleeding volume (in the PAST HOUR) | AFP level in maternal serum (ng/mL) | AFP level in vaginal blood specimen (ng/mL) | Final Diagnosis | Progesterone (maternal serum, ng/mL) | TSH (maternal serum, uIU/mL) | TSH (vaginal blood, uIU/mL) | Dilution factor calculated by TSH ratio | Original AFP concentration in vaginal blood (according to TSH dilution factor) | AFPvb/AFPms |
|---|---|---|---|---|---|---|---|---|---|
| Spotting | 4.54 | <0.5 | Threatened Miscarriage | 51.31 | 2.28 | 0.03 | 76.0 | NA | NA |
| 10-50 cc | 0.922 | <0.5 | Pregnancy of unknown location | 0.137 | 2.82 | 0.08 | 35.3 | NA | NA |
| over 100 cc | 4.67 | 739.2 | Inconclusive | 10.51 | 2.12 | 0.084 | 25.2 | 18,656.00 | 3,995 |
| Spotting | 6.75 | <0.5 | Threatened Miscarriage | 26.26 | 0.675 | 0.011 | 61.4 | NA | NA |
| 1-10 cc | 1.75 | <0.5 | spontaneously failed early PUL | 3.58 | 2.75 | 0.014 | 196.4 | NA | NA |
| 1-10 cc | 2.98 | <0.5 | Threatened Miscarriage | 17.5 | 0.458 | 0.005 | 91.6 | NA | NA |
| 1-10 cc | 2.33 | <0.5 | Threatened Miscarriage | 14.12 | 0.573 | 0.006 | 95.5 | NA | NA |
| 1-10 cc | 0.848 | <0.5 | Threatened Miscarriage | 11.3 | 0.615 | 0.012 | 51.3 | NA | NA |
| Spotting | 1.56 | <0.5 | Threatened Miscarriage | 25.02 | 0.133 | 0.008 | 16.6 | NA | NA |
| 10-50 cc | 2.03 | <0.5 | Complete Miscarriage | 4.52 | 2.56 | 0.094 | 27.2 | NA | NA |
| 1-10 cc | 1.51 | <0.5 | Threatened Miscarriage | 21.93 | 0.361 | 0.02 | 18.1 | NA | NA |
| 1-10 cc | 1.87 | <0.5 | Threatened Miscarriage | 6.37 | 0.78 | 0.011 | 70.9 | NA | NA |
| 10-50 cc | 3.07 | <0.5 | Pregnancy of unknown location | 4.17 | 1.11 | 0.037 | 30.0 | NA | NA |
| Spotting | 254.4 | 23.73 | incomplete AB, completed by POCs removal at the ED. | 1.75 | 0.926 | 0.024 | 38.6 | 915.58 | 4 |
| Spotting | 1.26 | <0.5 | Complete Miscarriage | 2.38 | 0.303 | 0.011 | 27.5 | NA | NA |
| 10-50 cc | 3.66 | <0.5 | Ectopic pregnancy | 44.6 | 0.741 | 0.006 | 123.5 | NA | NA |
| 10-50 cc | 4.03 | <0.5 | Threatened Miscarriage | 27.99 | 1.44 | 0.025 | 57.6 | NA | NA |
| over 100 cc | 25.57 | 10.9 | incomplete AB, completed by POCs removal at the OR. | 3.33 | 1.7 | 0.053 | 32.1 | 349.62 | 14 |
| 1-10 cc | 0.568 | <0.5 | Threatened Miscarriage | 51.7 | 3.64 | 0.016 | 227.5 | NA | NA |
| Spotting | 1.71 | <0.5 | Inconclusive | 11.8 | 7.2 | 0.02 | 360.0 | NA | NA |
| Spotting | 2.13 | <0.5 | PUL | 0.19 | 2.13 | 0.059 | 36.1 | NA | NA |
| 1-10 cc | 1.73 | <0.5 | Failing PUL (biochemical pregnancy) | 1.74 | 2.44 | 0.126 | 19.4 | NA | NA |
| over 100 cc | 3.82 | <0.5 | complete miscarriage with full expulsion of POCs from uterus and vagina vs. some POCs in vagina. | 9.06 | 1.17 | 0.129 | 9.1 | NA | NA |

TABLE 2-continued

| Estimated bleeding volume (in the PAST HOUR) | AFP level in maternal serum (ng/mL) | AFP level in vaginal blood specimen (ng/mL) | Final Diagnosis | Progesterone (maternal serum, ng/mL) | TSH (maternal serum, uIU/mL) | TSH (vaginal blood, uIU/mL) | Dilution factor calculated by TSH ratio | Original AFP concentration in vaginal blood (according to TSH dilution factor) | AFPvb/ AFPms |
|---|---|---|---|---|---|---|---|---|---|
| 50-100 cc | 2.11 | <0.5 | Complete miscarriage | 3.58 | 2.06 | 0.174 | 11.8 | NA | NA |
| 1-10 cc | 2.01 | 42.25 | Missed Miscarriage | 5.2 | 1.57 | 0.014 | 112.1 | 4,738.04 | 2,357 |
| Spotting | 2.27 | 2.46 | Complete Miscarriage but blood collected from POC specimen spontaneously evacuated | 5.43 | 0.873 | 0.038 | 23.0 | 56.5 | 24.9 |
| over 100 cc | 14.46 | 4.85 | Inconclusive | 5.32 | 0.263 | 0.177 | 1.5 | 7.2 | 0.5 |
| Spotting | 4.89 | <0.5 | Threatened Miscarriage | 37.35 | 1.28 | 0.008 | 160.0 | NA | NA |
| 50-100 cc | 4.38 | 0.653 | Missed Miscarriage | 12.69 | 1.11 | 0.152 | 7.3 | 4.8 | 1.1 |
| very minimal | 9.05 | <0.5 | Threatened Miscarriage | 38.67 | 3.67 | 0.006 | 611.7 | NA | NA |
| 1-10 cc | 2.18 | 47.58 | Inconclusive | 0.759 | 1.13 | 0.108 | 10.5 | 497.8 | 228.4 |
| Spotting | 2.91 | 0.609 | Threatened Miscarriage | 20.52 | 0.421 | 0.008 | 52.6 | 32.0 | 11.0 |
| Spotting | no sample | <0.5 | Threatened Miscarriage | no sample | no sample | 0.018 | NA | NA | NA |
| 10-50 cc | 2.54 | <0.5 | Threatened Miscarriage | 26.32 | 1.22 | 0.196 | 6.2 | NA | NA |
| over 100 cc | 1.28 | <0.5 | Inconclusive | 7.92 | 2.04 | 0.079 | 25.8 | NA | NA |
| 1-10 cc | 2.84 | <0.5 | Threatened Miscarriage | 34.19 | 1.64 | 0.016 | 102.5 | NA | NA |
| Spotting | 2.06 | <0.5 | Ectopic pregnancy | 1.23 | 0.317 | 0.016 | 19.8 #DIV/0! | NA | NA |
| Spotting | 3.48 | <0.5 | Threatened Miscarriage | 19.19 | 0.492 | 0.01 | 49.2 | NA | NA |
| 1-10 cc | 1.22 | <0.5 | Threatened Miscarriage | 6.96 | 0.867 | 0.023 | 37.7 | NA | NA |
| over 100 cc | 6.41 | 11.49 | Incomplete miscarriage | 2.5 | 4.42 | 0.831 | 5.3 | 61.11 | 10 |
| 1-10 cc | 1.92 | 0.963 | Missed Miscarriage | 9.79 | 1.11 | 0.057 | 19.5 | 18.75 | 10 |
| Amniotic fliud | 770.3 | 82120 | Termination of a viable IUP | 45.67 | 1.75 | 0.149 | 11.7 | 964,496.64 | 1,252 |
| 1-10 cc | 4.82 | 1041 | Termination of a viable IUP | 11.1 | 2.67 | 0.08 | 33.4 | 34,743.38 | 7,208 |
| 1-10 cc | 5.64 | 1686 | Termination of a viable IUP | 25.23 | 0.548 | 0.029 | 18.9 | 31,859.59 | 5,649 |
| Spotting | 11.89 | 2228 | Termination of a viable IUP | 13.14 | 0.045 | 0.035 | 1.3 | 2,864.57 | 241 |
| 1-10 cc | 3.9 | 4206 | Termination of a viable IUP | 21.23 | 1.35 | 0.107 | 12.6 | 53,066.36 | 13,607 |
| 1-10 cc | 3 | 12377 | Termination of a viable IUP | 11.98 | 0.875 | 0.075 | 11.7 | 144,398.33 | 48,133 |
| 1-10 cc | 21.34 | 1314 | Termination of a viable IUP | 11.71 | 0.374 | 0.058 | 6.4 | 8,473.03 | 397 |
| Spotting | 14.31 | 7561 | Termination of a viable IUP | 47.14 | 0.373 | 0.014 | 26.6 | 201,446.64 | 14,077 |
| Amniotic fluid | 36.99 | 4878 | Termination of a viable IUP | 32.16 | 1.36 | 0.23 | 5.9 | 28,843.83 | 780 |
| Amniotic fluid | 107.4 | 3991 | Termination of a viable IUP | 21.04 | 1.13 | 0.314 | 3.6 | 14,362.52 | 134 |
| 1-10 cc | 4.63 | 631.3 | Missed Miscarriage | 24.81 | 0.33 | 0.085 | 3.9 | 2,450.93 | 529 |
| Amniotic fluid | 98.93 | >100,000 | Termination of a viable IUP | 7.51 | 2.79 | 0.17 | 16.4 | NA | NA |
| Amniotic fluid | 729.5 | >100,000 | Missed Miscarriage | 4.89 | 0.854 | 0.195 | 4.4 | NA | NA |

TABLE 2-continued

| Estimated bleeding volume (in the PAST HOUR) | AFP level in maternal serum (ng/mL) | AFP level in vaginal blood specimen (ng/mL) | Final Diagnosis | Progesterone (maternal serum, ng/mL) | TSH (maternal serum, uIU/mL) | TSH (vaginal blood, uIU/mL) | Dilution factor calculated by TSH ratio | Original AFP concentration in vaginal blood (according to TSH dilution factor) | AFPvb/ AFPms |
|---|---|---|---|---|---|---|---|---|---|
| Spotting | 2 | 1.59 | Threatened Miscarriage, but AFP level is high because other embryo(s) are dissolving. | >60 | 1.63 | 0.01 | 163.0 | 259.17 | 130 |
| Spotting | 2.74 | <0.5 | Pregnancy of unknown location | 17.56 | 3.07 | 0.018 | 170.6 | | |

AFP lateral flow assay strips showed positive results in all maternal serum and vaginal blood (including reconstituted vaginal blood) specimens having AFP concentration above 30 ng/mL.

Discussion:

This study represents the first proof of concept that AFP and TSH can be extracted and detected in blood, including moist or dried blood, extracted from an absorbent substrate, such as feminine hygiene pads collected from women with $1^{st}$ or $2^{nd}$ trimester bleeding.

When AFPvb is detected (above 0.5 ng/mL), the likelihood of a failed intrauterine pregnancy is 89% (8 out of 9 cases) whereas this likelihood drops dramatically when AFPvb is undetectable (FIG. 6). Moreover, original AFPvb calculation (according to DF) is not mandatory in order to reach this conclusion.

Measurement of AFPvb may help to predict the fate of intrauterine pregnancy in the setting of $1^{st}$ or $2^{nd}$ trimester bleeding.

High AFP in vaginal blood confirms that embryonic/fetal tissue is/was in the uterus.

Low AFP in vaginal blood raises the concern that there is/was no pregnancy in the uterus (e.g., an ectopic pregnancy).

Conclusions:

In the cases of pregnancy of unknown location, intrauterine specimen can be actively evacuated, such as by D&C or by using a pipelle curette (or a similar tool). AFP level can be checked in the specimen evacuated from the uterus. If AFP level is relatively high, IUP is confirmed. If AFP level is relatively low (or undetected), there is no embryonic/fetal tissue in the uterus. Therefore, for example, pregnancy outside the uterus, a complete miscarriage, or an intrauterine complete mole should be suspected.

High AFP level in specimens passively evacuated from the uterus via the vaginal blood or in specimens actively evacuated from the uterus confirms the presence of embryonic/fetal tissue and therefore excludes the possibility of a complete mole.

Additionally, there is probably an absolute HIGH level of AFPvb when a miscarriage can be detected. In this case, AFP test strip embedded in a pad or dripped in the tube's solution would suffice. There is no need to sample maternal serum and calculate the DF. This would be a home test kit for miscarriage.

Recommended Actions/Treatments:

If AFP level is low in vaginal blood or in the specimen evacuated from the uterus (actively or passively), there is a concern for an ectopic pregnancy and therefore Methotrexate (and/or other cytotoxic drug(s)) administration, a diagnostic/operative laparoscopy, an open abdominal surgery, administration of intravenous fluid, or combination of these interventions is recommended. Additionally, administration of anti D antibodies is recommended for rh negative women due to the possibility of bleeding into the abdomen and exposure to embryonic/fetal antigens.

If AFP level is relatively high in the vaginal blood or in the specimen evacuated from the uterus (actively or passively), the pregnancy was/is likely to be in the uterus. Additionally, this intrauterine pregnancy has probably failed and therefore uterotonics (e.g. Misoprostol, Methergine, and Oxytocin), anti progesterone medications (e.g., Mifepristone or RU 486), a dilation and curettage procedure (D&C), hysteroscopy, administration of anti D antibodies, bedside manual vacuum aspiration of uterine contents, administration of intravenous fluid, or combination of these interventions is advised.

Diagnostic laparoscopy (a pelvic surgery) or any other surgery are considered an invasive procedure.

Methotrexate is considered a cytotoxic therapy/drug aimed at stopping the growth of pregnancy outside the uterus.

Folic and folinic acids can be a part of the multi dose Methotrexate administration regimen.

Intravenous fluid can include crystalloids and/or blood products.

In the case a gestational trophoblastic disease such as molar pregnancy (complete or partial mole) is diagnosed, Methotrexate and/or other cytotoxic/chemotherapeutic therapy is/are advised. A complete mole does not have embryonic tissue (i.e., anembryonic pregnancy).

Anti progesterone therapy (e.g., Mifepristone) has the potential to stop growth of embryonic and anembryonic (e.g., placenta only) pregnancy.

Treatment options for pregnancy of unknown location may include the following:

Pelvic surgery, cytotoxic therapy, dilation and curettage, aspiration of the uterine cavity, administration of uterotonics, aspiration of the abdominal cavity, administration of a progesterone antagonist, hysteroscopy, administration of intravenous fluid, injection of antibodies, administration of folic acid, administration of folinic acid, or combinations thereof.

Administration of intravenous fluids (crystalloids and/or blood products) is indicated when excessive bleeding occurs or is anticipated (for example during an incomplete miscarriage or when an ectopic pregnancy ruptures).

Example 5

Identification and Treatment of an Absence of Fetal or Embryonic Tissue in a Pregnant Subject According to some embodiments, the methods disclosed herein may be useful for evaluation and treatment of pregnancy of unknown location. A non-limiting example is provided as follows:

A pregnant patient presents with first trimester bleeding. Sampling the vaginal blood shows low level or undetectable AFP. This is an unwanted pregnancy and therefore a D&C is done. AFP is still low in the intrauterine specimen evacuated by D&C. Therefore, an ectopic pregnancy is suspected. Pelvic ultrasound is done but the pregnancy location cannot be identified. Intramuscular Methotrexate administration vs. a laparoscopic surgery are discussed with the patient. The patient lives two hours away from the hospital. Therefore, laparoscopy (a pelvic surgery) is chosen as the preferred treatment option. During the surgery, a mass is identified in the right fallopian tube. The mass is removed and biopsied. AFP level in the biopsied specimen is high. A right tubal ectopic pregnancy is confirmed (i.e., presence of embryonic/fetal tissue in the right tube) through the detection of high levels of AFP.

Devices Useful in the Method of the Present Invention

The concentration of an element of fetal or embryonic origin may be determined by any method known in the art, such as, but not limited to, quantification of a known marker of the element of fetal or embryonic origin.

Examples of such methods include a chemiluminescence immunoassay (for example, that produced by Beckman Coulter Inc., USA, as referred to above, for measurement of AFP concentration), enzyme-linked immunosorbent assay (ELISA), lateral flow assay, immunohistochemistry, or radioimmunoassay. Other methods can include use of a biorecognition molecule rather than an immunoassay.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

REFERENCES

1. Sarandakou A, Protonotariou E, Rizos D. Tumor markers in biological fluids associated with pregnancy. Crit Rev Clin Lab Sci 2007; 44:151-78.
2. Mizejewski G J. Levels of alpha-fetoprotein during pregnancy and early infancy in normal and disease states. Obstet Gynecol Surv 2003; 58:804-26.
3. Doubilet P M, Benson C B, Bourne T, et al. Diagnostic criteria for nonviable pregnancy early in the first trimester. The New England journal of medicine 2013; 369:1443-51.
4. Sajid M, Kawde A-N, Daud M. Designs, formats and applications of lateral flow assay: A literature review. Journal of Saudi Chemical Society 2015; 19:689-705.
5. Kolte A M, Bernardi L A, Christiansen O B, Quenby S, Farquharson R G, Goddijn M, et al. Terminology for pregnancy loss prior to viability: a consensus statement from the ESHRE early pregnancy special interest group. Hum Reprod. 2015; 30(3):495-8.
6. Mor A, Tal R, Haberman S, Kalgi B, Nasab S H, Minkoff H. Same-day confirmation of intrauterine pregnancy failure in women with first-and early second-trimester bleeding. Fertility and sterility. 2018 Jun. 1; 109(6):1060-4.

What is claimed is:

1. A method for identifying and treating a pregnancy devoid of uterine fetal or embryonic tissue in a subject, the method comprising
   determining a concentration of alpha-fetoprotein (AFP) in a specimen evacuated from the uterus of the subject;
   comparing said concentration of AFP to a reference value;
   wherein when said AFP concentration in said specimen evacuated from the uterus is below that of a reference value, absence of uterine fetal or embryonic tissue is indicated; and
   treating the subject in whom absence of uterine fetal or embryonic tissue is indicated by a procedure selected from the group consisting of pelvic surgery, cytotoxic therapy, dilation and curettage, aspiration of the uterine cavity, administration of uterotonics, aspiration of the abdominal cavity, administration of a progesterone antagonist, administration of intravenous fluid, injection of antibodies, administration of folic acid, administration of folinic acid, or combinations thereof.

2. The method of claim 1, wherein said reference value is 0.55 ng/mL.

3. The method of claim 1, wherein said specimen evacuated from the uterus of the subject is evacuated by an active procedure.

4. The method of claim 3, wherein said active procedure is selected from the group consisting of dilation and curettage, aspiration of uterine cavity, aspiration of the abdominal cavity and endometrial biopsy.

5. The method of claim 1, wherein said specimen evacuated from the uterus of the subject is evacuated by a passive procedure.

6. The method of claim 5, wherein said passive procedure comprises bleeding via the vagina of the subject.

7. The method of claim 1, wherein said specimen evacuated from the uterus is a liquid specimen.

8. The method of claim 7, wherein said liquid specimen comprises blood.

9. The method of claim 1, wherein said specimen evacuated from the uterus is a solid specimen.

10. The method of claim 9, wherein said solid specimen comprises endometrial tissue.

11. The method of claim 1, wherein said pregnancy devoid of uterine fetal or embryonic tissue is selected from the group consisting of an intrauterine anembryonic pregnancy, an ectopic pregnancy, a complete molar pregnancy and a complete miscarriage.

12. The method of claim 6, wherein said specimen evacuated from the uterus is collected on an absorbent material.

13. The method of claim 12, wherein said absorbent material is provided within a feminine hygiene pad.

14. The method of claim 12, further comprising isolating a portion of said absorbent material containing said specimen evacuated from the uterus; extracting said specimen from said portion of absorbent material in a solvent; wherein said concentration of AFP is determined in said solvent.

15. The method of claim 14, further comprising
obtaining a sample of maternal serum of the subject;
determining a concentration of thyroid stimulating hormone (TSH) in vaginal blood after extraction in said solvent (TSHvb);
determining a concentration of TSH in said maternal serum (TSHms);
calculating a dilution factor [DF] wherein DF=TSHms/TSHvb; and
calculating an original concentration of AFP in said specimen evacuated from the uterus prior to dilution in said solvent wherein said original concentration of AFP=concentration of AFP determined in said solvent× DF.

16. A method for identifying and treating pregnancy failure in a subject, the method comprising:
determining a concentration of fetal hemoglobin (HbF) in the vaginal fluid of the subject; and
comparing said concentration of said HbF to a reference value,
wherein when said concentration of said HbF in said vaginal fluid is higher than said reference value, pregnancy failure is indicated; and
treating the subject in whom pregnancy failure is indicated by a procedure selected from the group consisting of pelvic surgery, cytotoxic therapy, dilation and curettage, aspiration of the uterine cavity, administration of uterotonics, aspiration of the abdominal cavity, administration of a progesterone antagonist, administration of intravenous fluid, injection of antibodies, administration of folic acid, administration of folinic acid, or combinations thereof.

17. A method for identifying and treating an intrauterine pregnancy in a subject, the method comprising:
determining a level of fetal hemoglobin (HbF) in a specimen evacuated from the uterus of the subject; and
comparing said concentration of said HbF to a reference value,
wherein when said concentration of said HbF in said specimen is higher than said reference value, intrauterine pregnancy is indicated; and
treating the subject in whom intrauterine pregnancy is indicated by a procedure selected from the group consisting of pelvic surgery, cytotoxic therapy, dilation and curettage, aspiration of the uterine cavity, administration of uterotonics, aspiration of the abdominal cavity, administration of a progesterone antagonist, administration of intravenous fluid, injection of antibodies, administration of folic acid, administration of folinic acid, or combinations thereof.

* * * * *